United States Patent
Koop et al.

(10) Patent No.: US 8,002,883 B2
(45) Date of Patent: Aug. 23, 2011

(54) AMIDOALKYLAMINE-COMPRISING AZOLE COMPOSITIONS FOR PROTECTING INDUSTRIAL MATERIALS

(75) Inventors: Bernd Koop, Köln (DE); Martin Kugler, Leichlingen (DE); Andreas Böttcher, Köln (DE); Johannes Kaulen, Odenthal (DE)

(73) Assignee: LANXESS Deutschland GmbH, Leverkusen (DE)

( * ) Notice: Subject to any disclaimer, the term of this patent is extended or adjusted under 35 U.S.C. 154(b) by 0 days.

(21) Appl. No.: 12/792,907

(22) Filed: Jun. 3, 2010

(65) Prior Publication Data

US 2011/0030579 A1    Feb. 10, 2011

(30) Foreign Application Priority Data

Jun. 18, 2009    (EP) .................... 09163144

(51) Int. Cl.
| | |
|---|---|
| A01N 33/00 | (2006.01) |
| A01N 33/02 | (2006.01) |
| A01N 25/00 | (2006.01) |
| A01N 25/30 | (2006.01) |
| A01N 43/653 | (2006.01) |
| A01P 3/00 | (2006.01) |
| B27K 3/50 | (2006.01) |
| C09D 5/16 | (2006.01) |

(52) U.S. Cl. ............... 106/18.32; 514/359; 514/360
(58) Field of Classification Search ............ 106/18.32; 514/359, 360
See application file for complete search history.

(56) References Cited

U.S. PATENT DOCUMENTS

| | | | |
|---|---|---|---|
| 6,231,651 B1 | 5/2001 | Schultz et al. | |
| 6,527,981 B1 | 3/2003 | Tseng et al. | |
| 2004/0151749 A1 | 8/2004 | Hasebe et al. | |
| 2005/0080089 A1 | 4/2005 | Tiedink et al. | |

FOREIGN PATENT DOCUMENTS

| | | |
|---|---|---|
| WO | 93/02557 A1 | 2/1993 |
| WO | 19953274 A1 | 5/2001 |
| WO | 01/95720 A1 | 12/2001 |
| WO | 2008/068214 A2 | 6/2008 |

OTHER PUBLICATIONS

European Search Report from co-pending Application EP09163144 dated Jan. 12, 2010, 4 pages.
T.M. Muzyczko et al; "Fatty amidoamine derivatives: N,N-dimethyl-N-(3 alkylamidopropyl)amines and their salts" Journal of the American Oil Chemists' Society, Springer, Berlin, DE. Bd45, Nr. 11, Nov. 1, 1968, Seiten 720-725 XP-009090537; ISSN: 0003-021X.
F.C. Kull et al: "Mixtures of Quaternary Ammonium Compounds and Long-Chain Fatty Acids as Antifungal Agents" Applied Microbioloby, 1961, 9, 538-541.

*Primary Examiner* — Anthony Green
(74) *Attorney, Agent, or Firm* — Nicanor A. Kohncke

(57) ABSTRACT

Use of compositions comprising
a) at least one azole and
b) at least one amidoalkylamine of the formula (I), a salt and/or acid addition compound thereof,

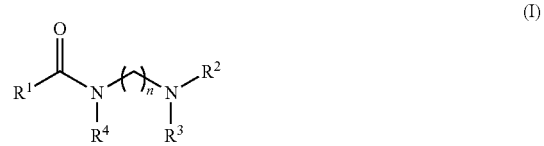

in which $R^1$ represents optionally substituted $C_1$-$C_{40}$-alkyl or $C_2$-$C_{40}$-alkenyl, $R^2$, $R^3$ and $R^4$ independently of one another represent hydrogen or $C_1$-$C_8$-alkyl and n represents an integer from 1 to 6 for protecting industrial materials against attack and/or destruction by microorganisms.

13 Claims, No Drawings

AMIDOALKYLAMINE-COMPRISING AZOLE COMPOSITIONS FOR PROTECTING INDUSTRIAL MATERIALS

The invention relates to the use of amidoalkylamine-comprising azole compositions for protecting industrial materials, corresponding compositions, industrial materials and a method for protecting industrial materials.

Active compounds for protecting wood, in particular against fungi, originate from a large number of compound classes. Of particular importance are azoles, in particular triazoles. However, individual active compounds do not cover the entire spectrum against the harmful fungi so that frequently combinations of active compounds have to be used, or the active compounds have to be employed in an appropriately high dosage.

In DE-A-19953274, for use in crop protection, specific fatty acid amidoamines are added to water-soluble and oil-soluble pesticides to stabilize the emulsion. They increase physical storage stability, and a corresponding higher activity (adjuvant effect) is described, too. However, the latter is optimum since generally it is impossible for unstable active compound preparations to have an optimum effect, if only for the reason that active compounds which have precipitated out or are no longer finely distributed naturally have a lower activity on application. However. DE-19953274 is not to be understood as an increased activity owing to the additive.

In WO 93/02557, the activity of azoles can be improved by addition of quaternary ammonium compounds or tertiary amine salts. However, these compounds have to be biocidally active for their part—i.e. they have to be active compounds (see p. 5, line 23 and lines 32-35). Accordingly, causally they act as biocides. Thus, these additives are to be considered as classic active compounds giving, together with others, classic active compound mixtures. However, not infrequently, further active compounds are also associated with disadvantages which have to be avoided for certain applications. However, an increased activity by additives which for their part are not active compounds is not described.

To overcome these weaknesses of the active compounds, various options of enhancing the activity have been investigated for the protection of materials, in particular for the protection of wood.

U.S. Pat. No. 6,231,651 describes the use of phenolic antioxidants for enhancing the activity of azoles in the protection of wood. However, the antioxidants, such as BHT, are employed in a very high excess of up to about 450:1 (based on the azole). This is a big disadvantage, since the enhanced activity is made more expensive by the large amounts of additive.

WO0071314 describes the use of amine oxides for enhancing the activity of azoles in the protection of wood. However, the fact that the amine oxides are water soluble results in the amine oxides being easily leached with water from the treated wood, the enhanced activity thus being lost again, WO95/17817, inter alia, describes, for some azoles, such as triadimefon, certain tertiary or quaternary amines in combination with chelating agents as activity enhancers against microorganisms, in particular phytopathogenic fungi (i.e. fungi encountered exclusively on plants). WO 01/95720, too, discloses activity enhancers for pesticides for the use in the field of plant protection. However, the fungicidal actions with or without activity enhancement described for crop protection cannot be transferred automatically to wood-destroying basidiomycetes, for example, in particular since, in the protection of industrial materials, the active compounds have to meet fundamentally different requirements with respect to stability, leaching behaviour, colour and compatibility with the fundamentally different formulation auxiliaries than in crop protection.

It was an object of the present invention to provide activity enhancers for azoles for the protection of industrial materials, in particular for the protection of wood, against attack and/or destruction by microorganisms, in particular wood-destroying basidiomycetes, preferably holobasidiomycetes.

Accordingly, surprisingly, a use of compositions comprising
a) at least one azole and
b) at least one amidoalkylamine of the formula (I), a salt and/or acid addition compound thereof

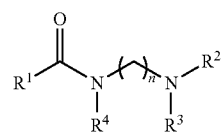

in which $R^1$ represents optionally substituted $C_1$-$C_{40}$-alkyl or $C_2$-$C_{40}$-alkenyl, $R^2$, $R^3$ and $R^4$ independently of one another represent hydrogen or $C_1$-$C_8$-alkyl
and n represents an integer from 1 to 6, has been found for protecting industrial materials against attack and/or destruction by microorganisms.

The azole used is preferably a fungicidally active azole, in particular at least one triazole or at least one imidazole. Particular preference is given to a triazole. In this respect, the composition for use in accordance with the invention is preferably employed as a microbicidal composition, in particular as a fungicidal composition.

Particularly preferred azoles are triazoles selected from the group consisting of azaconazole, bitertanol, bromuconazole, cyproconazole, diclobutrazol, difenoconazole, diniconazole, epoxyconazole, etaconazole, fenbuconazole, fluquinconazole, flusilazole, flutriafol, furconazole, hexaconazole, imibenconazole, ipconazole, myclobutanil, metconazole, penconazole, propiconazole, prothioconazole, simeconazole, tebuconazole, tetraconazole, triadimefon, triadimenol, tritconazole and uniconazole and their metal salts and acid adducts.

Particularly preferred imidazoles are, for example, clotrimazole, bifonazole, climbazole, econazole, fenpanil, imazalil, isoconazole, ketoconazole, lombazole, miconazole, pefurazoate, prochloraz, triflumizole and their metals salts and acid adducts.

Preference is given to using, in accordance with the invention, a composition comprising at least one azole selected from the group consisting of tebuconazole, propiconazole and cyproconazole and optionally a further azole selected from the group consisting of triadimenol and triadimefon.

Here, particular preference is given to the following azole combinations: tebuconazole and triadimefon, tebuconazole and propiconazole, tebuconazole and cyproconazole and propiconazole and cyproconazole.

A preferred composition for use in accordance with the invention comprises at least one compound of the formula (I), a salt and/or acid addition product thereof in which, preferably,
$R^1$ represents $C_2$-$C_{36}$-alkyl or $C_2$-$C_{36}$-alkenyl, $R^2$, $R^3$ and $R^4$ each independently of one another represent hydrogen or $C_1$-$C_4$-alkyl and
n represents a number from 1 to 4.

The composition for use in accordance with the invention very particularly preferably comprises at least one compound of the formula (I), a salt and/or acid addition product thereof in which
$R^1$ represents $C_5$-$C_{19}$-alkyl or $C_5$-$C_{19}$-alkenyl,
$R^2$ and $R^3$ each represent methyl,
$R^4$ represents hydrogen and
n represents 3.

The alkenyl radicals in the meaning of $R^1$ may contain one or more double bonds.

The compounds of the formula (I) may be employed individually or as mixtures. Particular preference is given to mixtures in which the compounds of the formula (I) have different radicals $R^1$. Particular preference is given to a mixture of compounds of the formula (I) comprising
5-10% by weight of (I) where $R^1$=an alkyl radical of octanoic acid, i.e. $C_7H_{15}$
5-9% by weight of (I) where $R^1$=an alkyl radical of decanoic acid. i.e. $C_9H_{19}$
41-53% by weight where $R^1$=an alkyl radical of dodecanoic acid
16-21% by weight where $R^1$=an alkyl radical of tetradecanoic acid
8-12% by weight of (I) where $R^1$=an alkyl radical of hexadecanoic acid
5-10% by weight of (I) where $R^1$=an alkenyl radical of oleic acid,
where the other radicals $R^2$ to $R^4$ and n of formula (I) have the above meaning. Particularly preferably, n=3, $R^2$ and $R^3$ each represent methyl and $R^4$ represents hydrogen.

The mixture may also comprise further amounts of compounds (I) where $R^1$=radicals of other fatty acids.

An example that may be mentioned is from 0 to 5% by weight of (I) where $R^1$=an alkenyl radical of linoleic acid.

An example of a compound of the formula (I) whose radical $R^1$ is based on coconut oil of the above $R^1$ mixture is the product Adsee® C80W from Akzo Nobel.

The azole of component a) employed is preferably employed in a weight ratio of from 50:1 to 1:50, in particular from 10:1 to 1:10, particularly preferably from 5:1 to 1:5, to a compound of component b). Component b) is preferably employed in a ratio of from 0.5:1 to 8:1, in particular from 2:1 to 5:1, to component a).

The compositions used in accordance with the invention can be employed in solid or liquid form. Suitable are formulations such as solutions, emulsions, suspensions, powders, granules, pastes, aerosols, and also microencapsulations in polymeric substances.

Preferred for use in accordance with the invention are compositions comprising water and/or an organic solvent. If the extender used is water, it is also possible to employ suitable organic solvents, i.e. organic solvents which are miscible with water forming a single phase, as auxiliary solvents.

Suitable organic solvents are, for example, aromatics, such as xylene, toluene or alkylnaphthalenes, chlorinated aromatics or chlorinated aliphatic hydrocarbons, such as chlorobenzenes, chloroethylenes) or methylene chloride, aliphatic hydrocarbons, such as cyclohexane or paraffins, for example mineral oil fractions (white spirit, Shellsol® D60 from Shell Chemical), monohydric alcohols, such as, for example, ethanol, isopropanol and butanol, polyhydric alcohols, such as, for example, glycerol, pentaerythritol, polyvinyl alcohol (for example Mowiol® from Kuraray), glycols, such as, for example, ethylene glycol and propylene glycol, oligoglycols and polyglycols, ethers of oligoglycols, such as, for example, dipropylene monomethyl ether for example Dowanol© TPM from Dow), ethers and esters of alcohols, such as 2,2,4-trimethyl-1,3-pentanediol mono(2-methylpropionate) (corresponds to Texanol® from Eastman), ketones, such as acetone, methyl ethyl ketone, methyl isobutyl ketone or cyclohexanone, in particular strongly polar aprotic solvents, such as dimethylformamide and dimethyl sulphoxide, and also, for example, fully etherified glycols, oligoglycols and polyglycols, such as, for example, ethylene glycol dibutyl ether, etherified polyols and esterified polyols, esters of mono- and polybasic carboxylic acids, for example diisobutyl adipate, diisobutyl maleate (for example Rhodiasolv® DIB).

However, the organic solvents mentioned may also preferably be used without or at least with only little water. In addition to components a) and b), the composition preferably comprises a solvent, in particular a solvent consisting to more than 95% by weight, preferably more than 98% by weight, of at least one organic solvent. Preferred is in particular a polar aprotic solvent, such as dimethylformamide or dimethyl sulphoxide, and also, for example, fully etherified glycols, oligoglycols and polyglycols, etherified polyols and esterified polyols, esters of mono- and polybasic carboxylic acids, for example diisobutyl adipate, diisobutyl maleate (for example Rhodiasolv® DIE).

The composition according to the invention may furthermore comprise, as further ingredients, adhesives, such as carboxymethylcellulose, natural and synthetic pulverulent, granular or latex-like polymers, such as gum arabic, polyvinyl alcohol, polyvinyl acetate, and also natural phospholipids, such as cephalins and lecithins, and synthetic phospholipids, and also mineral and vegetable oils, and also emulsifiers and/or foam-formers, such as, for example, nonionic and anionic emulsifiers, such as polyoxyethylene fatty esters (for example castor oil ethoxylate), polyoxyethylene fatty alcohol ethers, alkylaryl polyglycol ethers, alkylsulphonates, alkyl sulphates, aryl sulphonates and also protein hydrolysates. Suitable dispersants are, for example, lignosulphite waste liquors and methylcellulose.

In addition to the components a) and b) mentioned above, the composition employed preferably comprises at least one polar organic solvent, in particular 2,2,4-trimethyl-1,3-pentanediol mono-(2-methylpropionate), such as Texanol®, and at least one emulsifier, in particular a polyoxyethylene fatty ester, preferably castor oil ethoxylate, and, if appropriate, water.

The composition employed preferably comprises a chelating agent in an amount of less than 0.01 mol, preferably less than 0.001 mol, per mole of the compound of the formula (I) employed.

The compositions may furthermore comprise colorants, such as inorganic pigments, for example iron oxide, titanium oxide, Prussian blue, copper oxide, and organic dyes, such as alizarin, azo and metal phthalocyanine dyes.

The composition employed generally comprises preferably from 0.1 to 95% by weight of components a) and b), preferably from 0.5 to 90% by weight.

The compositions for use in accordance with the invention may also comprise further active compounds for example fungicides, bactericides and/or insecticides, for example to widen the activity spectrum or to prevent the development of resistance. In many cases, synergistic effects are obtained, i.e. the efficacy of combined active compounds is greater than the efficacy of the individual components.

Particularly favourable mixing partners are, for example, the following compounds:
pyridines and pyrimidines such as:
ancymidol, buthiobate, fenarimol, mepanipyrin, nuarimol, pyroxyfur, triamirol;

succinate dehydrogenase inhibitors such as:
benodanil, bixafen, boscalid, carboxim, carboxim sulphoxide, cyclafluramid, fenfuram, flutanil, furametpyr, furcarbanil, furmecyclox, mebenil, mepronil, methfuroxam, metsulfovax, nicobifen, pyrocarbolid, oxycarboxin, Shirlan, Seedvax;
naphthalene derivatives such as:
terbinafine, naftifine, butenafine, 3-chloro-7-(2-aza-2,7,7-trimethyloct-3-en-5-yne);
sulphenamides such as:
dichlofluanid, tolylfluanid, folpet, fluorofolpet; captan, captofol;
benzimidazoles such as:
carbendazim, benomyl, fuberidazole, thiabendazole or their salts;
morpholine derivatives such as:
aldimorph, dimethomorph, dodemorph, falimorph, fenpropidin, fenpropimorph, tridemorph, trimorphamid and their aryls salts such as, for example, p-toluenesulphonic acid and p-dodecylphenylsulphonic acid;
benzothiazoles such as:
2-mercaptobenzothiazole;
benzothiophene dioxides such as:
N-cyclohexyl-benzo[b]thiophenecarboxamide S,S-dioxide;
benzamides such as:
2,6-dichloro-N-(4-trifluoromethylbenzyl)benzamide, tecloftalam;
boron compounds such as:
boric acid, boric ester, borax;
formaldehyde and formaldehyde-releasing compounds such as:
benzyl alcohol mono(poly)hemiformal, n-butanol hemiformal, dazomet, ethylene glycol hemiformal, hexahydro-S-triazine, hexamethylenetetramine, N-hydroxymethyl-N'-methylthiourea, N-methylolchloroacetamide, oxazolidine, paraformaldehyde, taurolin, tetrahydro-1,3-oxazine. N-(2-hydroxypropyl)aminemethanol, tetramethylolacetylenediurea;
isothiazolinones such as:
N-methylisothiazolin-3-one, 5-chloro-N-methylisothiazolin-3-one, 4,5-dichloro-N-octylisothiazolin-3-one, 5-chloro-N-octylisothiazolinone. N-octylisothiazolin-3-one, 4,5-trimethyleneisothiazolinones, 4,5-benzoisothiazolinones;
aldehydes such as:
cinnamaldehyde, formaldehyde, glutardialdehyde, 3-bromocinnamaldehyde, o-phthaldialdehyde;
thiocyanates such as:
thiocyanatomethylthiobenzothiazole, methylenebisthiocyanate;
quaternary ammonium compounds and guanidines such as:
benzalkonium chloride, benzyldimethyltetradecylammonium chloride, benzyldimethyldodecylammonium chloride, dichlorobenzyldimethylalkylammonium chloride, didecyldimethylammonium chloride, dioctyldimethylammonium chloride. N-hexadecyltrimethylammonium chloride, 1-hexadecylpyridinium chloride, iminoctadine tris(albesilate);
iodine derivatives such as:
diiodomethyl p-tolyl sulphone, 3-iodo-2-propynyl alcohol, 4-chlorophenyl-3-iodopropargylformal, 3-bromo-2,3-diiodo-2-propenyl ethylcarbamate, 2,3,3-triiodoallyl alcohol, 3-bromo-2,3-diiodo-2-propenyl alcohol, 3-iodo-2-propynyl n-butylcarbamate, 3-iodo-2-propynyl n-hexylcarbamate, 3-iodo-2-propynyl cyclohexylcarbamate, 3-iodo-2-propynyl phenylcarbamate;
phenols such as:
tribromophenol, tetrachlorophenol, 3-methyl-4-chlorophenol, 3,5-dimethyl-4-chlorophenol, dichlorophene, 2-benzyl-4-chlorophenol, triclosan, diclosan, hexachlorophene, p-hydroxybenzoic esters, o-phenylphenol, m-phenylphenol, p-phenylphenol 4-(2-tert-butyl-4-methylphenoxy)phenol, 4-(2-isopropyl-4-methylphenoxy)phenol, 4-(2,4-dimethylphenoxy)phenol and their alkali metal salts and alkaline earth metal salts;
microbicides with an activated halogen group such as:
bronopol, bronidox, 2-bromo-2-nitro-1,3-propanediol, 2-bromo-4'-hydroxyacetophenone, 1-bromo-3-chloro-4,4,5,5-tetramethyl-2-imidazolidinone, β-bromo-β-nitrostyrene, chloracetamide, chloramine T, 1,3-dibromo-4,4,5,5-tetramethyl-2-imidazolidinone, dichloramine T, 3,4-dichloro-(3H)-1,2-dithiol-3-one, 2,2-dibromo-3-nitrilepropionamide, 1,2-dibromo-2,4-dicyanobutane, halane, halazone, mucochloric acid, phenyl (2-chlorocyanovinyl) sulphone, phenyl (1,2-dichloro-2-cyanovinyl) sulphone, trichloroisocyanuric acid;
pyridines such as:
1-hydroxy-2-pyridinethione (and their Cu, Na, Fe, Mn, Zn salts), tetrachloro-4-methylsulphonylpyridine, pyrimethanol, mepanipyrim, dipyrithion, 1-hydroxy-4-methyl-b'(2,4,4-trimethylpentyl)-2(1H)pyridine;
methoxyacrylates or similar such as:
azoxystrobin, dimoxystrobin, fluoxastrobin, kresoxim-methyl, metominostrobin, orysastrobin, picoxystrobin, pyraclostrobin, trifloxystrobin;
metal soaps such as:
salts of the metals tin, copper and zinc with higher fatty acids, resin acids, naphthenoic acids and phosphoric acid, such as, for example, tin naphthenate, tin octoate, tin 2-ethylhexanoate, tin oleate, tin phosphate, tin benzoate, copper naphthenate, copper octoate, copper 2-ethylhexanoate, copper oleate, copper phosphate, copper benzoate, zinc naphthenate, zinc octoate, zinc 2-ethylhexanoate, zinc oleate, zinc phosphate, zinc benzoate;
metal salts such as:
salts of the metals tin, copper, zinc, and also chromates and dichromates, such as, for example, copper hydroxycarbonate, sodium dichromate, potassium dichromate, potassium chromate, copper sulphate, copper chloride, copper borate, zinc fluorosilicate, copper fluorosilicate;
oxides such as:
oxides of the metals tin, copper and zinc, such as, for example, tributyltin oxide, $Cu_2O$, CuO, ZnO;
oxidizing agents such as:
hydrogen peroxide, peracetic acid, potassium persulphate;
dithiocarbamates such as:
cufraneb, ferban, potassium N-hydroxymethyl-N'-methyldithiobarbamate, sodium dimethyldithiocarbamate, potassium dimethyldithiocarbamate, macozeb, maneb, metam, metiram, thiram, zineb, ziram;
nitriles such as:
2,4,5,6-tetrachloroisophthalonitrile, disodium cyanodithioimidocarbamate;
quinolines such as:
8-hydroxyquinoline and their copper salts;
other fungicides and bactericides such as:
bethozaxin, 5-hydroxy-2(5H)furanone, 4,5-benzodithiazolinone, 4,5-trimethylenedithiazolinone, N-(2-p-chlorobenzoylethyl)hexaminium chloride, 2-oxo-2-(4-hydroxyphenyl) acetohydroxycinnamoyl chloride, tris-N-(cyclohexyldiazeniumdioxy)aluminium, N-(cyclohexyldiazeniumdioxy)tributyltin or its potassium salts, bis-N-(cyclohexyldiazeniumdioxy)copper; iprovalicarb, fenhexamide, spiroxamine, carpropamid, diflumetorin, quinoxyfen, famoxadone, polyoxorim, acibenzolar S-methyl, furametpyr, thifluzamide, methalaxyl-M, benthiavalicarb, metrafenone, cyflufenamid, tiadinil, tea tree oil, phenoxyethanol, Ag, Zn or Cu-containing zeolites alone or incorporated into polymeric materials.

Insecticides:

abamectin, acephate, acetamiprid, acetoprole, acrinathrin, alanycarb, aldicarb, aldoxycarb, aldrin, allethrin, alpha-cypermethrin, amidoflumet, amitraz, avermectin, azadirachtin, azinphos A, azinphos M, azocyclotin,

*Bacillus thuringiensis*, barthrin, 4-bromo-2(4-chlorophenyl)-1-(ethoxymethyl)-5-(trifluoromethyl)-1H-pyrrole-3-carbonitrile, bendiocarb, benfuracarb, bensultap, betacyfluthrin, bifenthrin, bioresmethrin, bioallethrin, bistrifluoron, bromophos A, bromophos M, bufencarb, buprofezin, butathiophos, butocarboxim, butoxycarboxim, cadusafos, carbaryl, carbofuran, carbophenothion, carbosulfan, cartap, quinomethionate, cloethocarb, 4-chloro-2-(2-chloro-2-methylpropyl)-5-[(6-iodo-3-pyridinyl)methoxy]-3(2H)-pyridazinone (CAS-RN: 120955-77-3), chlordane, chlorethoxyfos, chlorfenapyr, chlorfenvinphos, chlorfluazuron, chlormephos, N-[(6-chloro-3-pyridinyl)methyl]-N'-cyano-N-methylethaneimidamide, chlorpicrin, chlorpyrifos A, chlorpyrifos M, cis-resmethrin, clocythrin, clothiazoben, cypophenothrin, clofentezin, coumaphos, cyanophos, cycloprothrin, cyfluthrin, cyhalothrin, cyhexatin, cypermethrin, cyromazin, decamethrin, deltamethrin, demeton M, demeton S, demeton-S-methyl, diafenthiuron, dialiphos, diazinon, 1,2-dibenzoyl-1(1,1-dimethyphydrazine, DNOC, dichlofenthion, dichlorvos, dicliphos, dicrotophos, difethialone, diflubenzuron, dimethoate, 3,5-dimethylphenyl methylcarbamate, dimethyl(phenyl)silylmethyl-3-phenoxybenzyl ether, dimethyl (4-ethoxyphenyl)silylmethyl-3-phenoxybenzyl ether, dimethylvinphos, dioxathion, disulfoton, eflusilanate, emamectin, empenthrin, endosulfan, EPN, esfenvalerate, ethiofencarb, ethion, ethofenprox, etrimphos, etoxazole, etobenzanid, fenamiphos, fenazaquin, fenbutatin oxide, fenfluthrin, fenitrothion, fenobucarb, fenothiocarb, fenoxycarb, fenpropathrin, fenpyrad, fenpyroximate, fensulfothion, fenthion, fenvalerate, fipronil, flonicamid, fluacrypyrim, fluazuron, flucycloxuron, flucythrinate, flufenerim, flufenoxuron, flufluypyrazofos, flufenzine, flumethrin, flufenprox, fluvalinate, fonophos, formethanate, formothion, fosmethilan fosthiazate, fubfenprox, furathiocarb, halofenocid, HCH, (CAS RN: 58-89-9), heptenophos, hexaflumuron, hexythiazox, hydramethylnon, hydroprene, imidacloprid, imiprothrin, indoxycarb, iodfenfos, iprinomectin, iprobenfos, isazophos, isoamidophos, isofenphos, isoprocarb, isoprothiolane, isoxathion, ivermectin, lama-cyhalothrin, lufenuron, kadedrin, lambda-cyhalothrin, lufenuron, malathion, mecarbam, mervinphos, mesulfenphos, metaldehyde, methacrifos, methamidophos, methidathion, methiocarb, methomyl, metalcarb, milbemectin, monocrotophos, moxiectin, naled, NI 125, nicotine, nitenpyram, noviflumuron, omethoate, oxarnyl, oxydernethon M, oxydeprofos, parathion A, parathion M, penfluoron, permethrin, 2-(4-phenoxyphenoxy)ethyl ethylcarbamate, phenthoate, phorate, phosalon, phosmet, phosphamidon, phoxim, pirimicarb, pirimiphos M, pirimiphos A, prallethrin, profenophos, promecarb, propaphos, propoxur, prothiophos, prothoate, pymetrozin, pyrachlophos, pyridaphenthion, pyresmethrin, pyrethrum, pyridaben, pyridalyl, pyrimidifen, pyriproxifen, pyrithiobac-sodium, quinalphos, resmethrin, rotenone, salithion, sebufos, sitafluofen, spinosad, spirodiclofen, spiromesifen, sulfotep, sulprofos, tau-fluvalinate, taroils, tebufenozide, tebufenpyrad, tebupirimphos, teflubenzuron, tefluthrin, temephos, terbam, terbufos, tetrachlorvinphos, tetramethrin, tetramethacarb, thiacloprid, thiafenox, thiamethoxam, thiapronil, thiodicarb, thiofanox, thiazophos, thiocyclam, thiomethon, thionazin, thuringiensin, tralomethrin, transfluthrin, triarathen, triazophos, triazamate, triazuron, trichlorfon, triflumuron, trimethacarb, vamidothion, xylylcarb, zetamethrin;

herbicides and algicides:

acetochlor, acifluorfen, aclonifen, acrotein, alachlor, alloxydim, ametryn, amidosulfuron, amitrole, ammonium sulphamate, anilofos, asulam, atrazine, azafenidin, aziptrotryne, azimsulfuron, benazotin, benfluratin, benfuresate, bensulfuron, bensulfide, bentazone, benzofencap, benzthiazuron, bifenox, bispyribac, bispyribac-sodium, borax, bromacil, bromobutide, bromofenoxim, bromoxynil, butachlor, butamifos, butralin, butylate, bialaphos, benzoyl-prop, bromobutide, butroxydim, carbetamide, carfentrazone-ethyl, carfenstrole, chlomethoxyfen, chloramben, chlorbromuron, chlorflurenol, chloridazon, chlorimuron, chlomitrofen, chloroacetic acid, chloransulam-methyl, cinidon-ethyl chlorotoluron, chloroxuron, chlorpropham, chlorsulfuron, chlorthal, chlorthiamid, cinmethylin, cinofutsuron, clefoxydim, clethodim, clomazone, chlomeprop, clopyralid, cyanamide, cyanazine, cycloate, cycloxydim, chloroxynil, clodinafop-propargyl, cumyluron, clometoxyfen, cyhatofop, cyhatofop-butyl, clopyrasuluron, cyclosulfamuron, diclosulam, dichlorprop, dichlorprop-P, diclofop, diethatyl, difenoxuron, difenzoquat, diflufenican, diflufenzopyr, dimefuron, dimepiperate, dimethachlor, dimethipin, dinitramine, dinoseb, dinoseb acetate, dinoterb, diphenamid, dipropetryn, diquat, dithiopyr, diduron, DNOC, DSMA, 2,4-D, daimuron, dalapon, dazomet, 2,4-DB, desmedipham, desmetryn, dicamba, dichlobenil, dimethamid, dithiopyr, dimethametryn, eglinazine, endothal, EPTC, esprocarb, ethalfluralin, ethidimuron, ethofumesate, ethobenzanid, ethoxyfen, ethametsulfuron, ethoxysulfuron, fenoxaprop, fenoxaprop-P, fenuron, flamprop, flamprop-M, flazasulfuron, fluazifop, fluazifop-P, fuenachlor, fluchloralin, flufenacet, flumeturon, fluorocglycofen, fluoronitrofen, flupropanate, flurenol, fluridone, fluorochloridone, fluoroxypyr, fomesafen, fosamine, fosametine, flamprop-isopropyl, flamprop-isopropyl-L, flufenpyr flumiclorac-pentyl, flumipropyn, flumioxzim, flurtamone, flumioxzim, flupyrsulfuron-methyl, fluthiacet-methyl, glyphosate, glufosinate-ammonium haloxyfop, hexazinone, imazamethabenz, isoproturon, isoxaben, isoxapyrifop, imazapyr, imazaquin, imazethapyr, ioxynil, isopropalin, imazosulfuron, imazomox, isoxaflutole, imazapic, ketospiradox, lactofen, lenacil, linuron, MCPA, MCPA-hydrazide, MCPA-thioethyl, MCPB, mecoprop, mecoprop-P, mefenacet, mefluidide, mesosulfuron, metam, metamifop, metarnitron, metazachlor, methabenzthiazuron, methazole, methoroptryne, methyldymron, methyl isothiocyanate, metobromuron, metoxuron, metribuzin, metsulfuron, molinate, monalide, monalinuron. MSMA, metolachlor, metosulam, metobenzuron,
naproanilide, napropamide, naptalam, neburon, nicosulfuron, norflurazon, sodium chlorate, oxadiazon, oxyfluorfen, oxysulfuron, orbencarb, oryzalin, oxadiargyl.
propyzamide, prosulphocarb, pyrazolate, pyrazolsulfuron, pyrazoxyfen, pyribenzoxim, pyributicarb, pyridate, paraquat, pebulate, pendimethalin, pentachlorophenol, pentoxazone, pentanochlor, petroleum oils, phenmedipham, picloram, piperophos, pretilachlor, primisulfuron, prodiamine, profoxydim, prometryn, propachlor, propanil, propaquizafob, propazine, propham, propisochlor, pyriminobacmethyl, pelargonic acid, pyrithiobac, pyraflufen-ethyl,
quinmerac, quinocloamine, quizalofop, quizalofop-P, quinchlorac,
rimsulfuron
sethoxydim, sifuron, simazine, simetryn, sulphosulfuron, sulfometuron, sulfentrazone, sulcotrione, sulphosate,
tar oils, TCA, TCA-sodium, tebutam, tebuthiuron, terbacil, terbumeton, terbuthylazine, terbutryn, thiazafluoron, thifensulfuron, thiobencarb, thiocarbazil, tralkoxydim, triallate, triasulphuron, tribenuron, triclopyr, tridiphane, trietazine, trifluoralin, tycor, thdiazimin, thiazopyr, triflusulfuron,
vernolate.

In the present context, industrial materials are to be understood as meaning non-living materials which have been prepared for use in industry. Industrial materials which are to be protected by the present invention against microbial change or destruction are, for example, adhesives, sizes, paper and board, textiles, leather, wood, timber products, wood-plastic composites, paints, synthetic articles, cooling lubricants and other materials which can be attacked or destroyed by microorganisms. Parts of production plants, for example cooling-water circuits, which may be impaired by the multiplication of microorganisms may also be mentioned as materials to be protected. Industrial materials in the context of the present invention are preferably adhesives, sizes, paper and board, leather, wood, timber products, wood-plastic composites, paints, cooling lubricants and heat transfer liquids; particularly preferred industrial materials are wood, timber products and wood-plastic composites (WPC).

Wood is to be understood as meaning, in particular: construction timber, wooden beams, railway sleepers, bridge components, jetties, vehicles made of wood, boxes, pallets, containers, telephone poles, wooden fences, wood lagging, windows and doors made of wood, joiners work and wood-based materials used in domestic construction or carpentry and joinery.

Timber products are to be understood as meaning, in particular: plywood, chipboard, fibre board, oriented strand board (OSB) or composite board.

Wood-plastic composites are to be understood as meaning, in particular: thermoplastically processable composites consisting of wood, plastic and additives.

Wood is particularly preferred.

Microorganisms which may be mentioned as causing degradation or modification of the industrial materials are, for example, bacteria, fungi, yeasts, algae and slime organisms. The mixtures according to the invention preferably act against wood-destroying basidiomycetes, preferably holobasidiomycetes.

Here, mention may be made, in particular, of fungi of the following genera:
*Coniophora*, such as *Coniophora puetana*,
*Lentinus*, such as *Lentinus tigrinus*,
*Polyporus*, such as *Polyporus versicolor*,
*Gloeophyllum*, such as *Gloeophyllum trabeum*,
*Poria*, such as *Poria placenta*,
*Stereum*, such as *Stereum sanguinolentum*.

In addition, the compositions to be used according to the invention act against wood-destroying and soft rot-causing ascomycetes and associated deuteromycetes, such as, for example,
species of the genus *Glenospora*, such as *Glenospora graphii*,
species of the genus *Chaetomium*, such as *Chaetomium globosum*,
species of the genus *Humicola*, such as *Humicola grisea*,
species of the genus *Petriella*, such as *Petriella setifera*,
species of the genus *Trichurus*, such as *Trichurus spiralis*,
species of the genus *Lecythophora*, such as *Lecythophora mutabilis*
species of the genus *Sclerophoma*, such as *Sclerophoma pityophila*
species of the genus *Aureobasidium*, such as *Aureobasidium pullulans*

Surprisingly, it has now been found that, by the use according to the invention, it is possible to increase the activity of azoles, thus reducing weaknesses in activity, so that it is possible to use less active compound or to cover a broader spectrum of harmful fungi.

The invention furthermore relates to compositions comprising
a1) at least one azole selected from the group consisting of azaconazole, bitertanol, bromuconazole, cyproconazole, diclobutrazol, difenoconazole, diniconazole, epoxyconazole, etaconazole, fenbuconazole, fluquinconazole, flusilazole, flutriafol, furconazole, hexaconazole, imibenconazole, ipconazole, myclobutanil, metconazole, penconazole, propiconazole, prothioconazole, simeconazole, tebuconazole, tetraconazole, triticonazole and uniconazole and their metal salts and acid adducts;
a2) optionally one azole selected from the group consisting of triadimenol and triadimefon;
b) at least one amidoalkylamine of the formula (I), a salt and/or acid addition compound thereof,

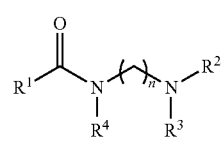

in which $R^1$ represents optionally substituted $C_1$-$C_{40}$-alkyl or $C_2$-$C_{40}$-alkenyl, $R^2$, $R^3$ and $R^4$ independently of one another represent hydrogen or $C_1$-$C_8$-alkyl and n represents an integer from 1 to 6.

Preferred compositions according to the invention comprise at least one azole selected from the group consisting of tebuconazole, propiconazole and cyproconazole and optionally a further azole selected from the group consisting of triadimenol and triadimefon.

Otherwise, the preferred ranges for the compositions used according to the invention also apply to the compositions according to the invention.

The invention furthermore relates to a process for preparing the composition according to the invention.

The composition according to the invention can be prepared, for example, by mixing the individual components, optionally with extenders, i.e. liquid solvents, optionally using further additives.

The invention furthermore relates to industrial materials, in particular wood, timber products or wood/plastic composites, comprising
a) at least one azole and
b) at least one amidoalkylamine of the formula (I), a salt and/or acid addition compound thereof,

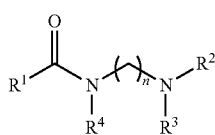

(I)

in which $R^1$ represents optionally substituted $C_2$-$C_{40}$-alkyl or $C_2$-$C_{40}$-alkenyl, $R^2$, $R^3$ and $R^4$ independently of one another represent hydrogen or $C_1$-$C_8$-alkyl and n represents an integer from 1 to 6.

Moreover, the invention relates to a method for protecting industrial materials against attack and/or destruction by microorganisms, characterized in that at least one composition comprising
a) at least one azole and
b) at least one amidoalkylamine of the formula (I), a salt and/or acid addition compound thereof,

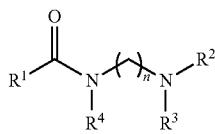

(I)

in which $R^1$ represents optionally substituted $C_2$-$C_{40}$-alkyl or $C_2$-$C_{40}$-alkenyl, $R^2$, $R^3$ and $R^4$ independently of one another represent hydrogen or $C_1$-$C_8$-alkyl is allowed to act on the microorganism or its habitat.

This method is to be considered as equivalent to the use according to the invention. Otherwise, all preferred ranges for the use or the composition according to the invention also apply to this method.

In the method according to the invention or in the use, the compositions are preferably applied to the industrial material by painting, drenching, spraying, impregnating or in a different way.

In the case of wood and timber products, preference is given to industrial impregnation processes, for example the vacuum, double vacuum, vacuum pressure or pressure process.

The amount of drench solution taken up by the wood depends on the process. In the vacuum pressure process, the wood preferably takes up 200-700 kg of drench solution per m³ of wood, in the double vacuum process preferably 20-40 kg/m³. The impregnation time depends on the process, in the pressure process it is, for example, from 0.5 to 6 hours, in the double vacuum process from 3 to 60 min. With preference, based on the active compound employed, from 10 to 500 g, preferably from 50 to 400 g, in particular from 100 to 350 g, preferably from 100 to 250 g, of active compound and additionally activity enhancer and optionally further additives are used per m³ of wood.

Wood-plastic composites can be prepared, for example, by mixing wood particles, a thermoplastic polymer and the compositions with input of thermal energy, in particular by extrusion or injection moulding.

EXAMPLES

Example 1

Combinations of Tebuconazole and Amidoalkylamine Against the Wood-Destroying Fungus *Gloeophyllum trabeum*

Mycelium pieces were punched out of a colony of the wood-destroying fungus *Gloeophyllum trabeum* and incubated at 26° C. on a malt extract/peptone-containing nutrient agar. The hyphae growth with and without added active compound and/or amidoalkylamine was compared. The minimum inhibitory concentration (MIC) stated is the concentration at which the radial hyphae growth is suppressed completely (incubation time: about 1 week depending on the fungal growth of the comparative sample without active compound).

The amidoalkylamine of the formula (I) used in all examples was a compound of the formula

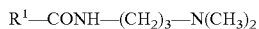

where
$R^1$ represents a mixture of various fatty acid radicals; the compound of the formula (I) thus being used as a mixture of the following compositions:

5-10% by weight of (I) where $R^1$=an alkyl radical of octanoic acid 5-9% by eight of (I) where $R^1$=an alkyl radical of decanoic acid 41-53% by weight where $R^1$=an alkyl radical of dodecanoic acid 16-21% by weight where $R^1$=an alkyl radical of tetradecanoic acid 8-12% by weight of (I) where $R^1$=an alkyl radical of hexadecanoic acid 5-10% by weight of (I) where $R^1$=an alkenyl radical of oleic acid.

This amidoalkylamine mixture (hereinbelow additive I) was used in an 80% strength form of the commercial product Adsee® C80/W from Akzo Nobel which comprises, as remainder, water and propylene glycol.

The synergism was determined by the method described by Kull et al. (F. C. Kull, P. C. Eismann, H. D. Sylvestrowicz, R. L. Mayer, Applied Microbiology 1961, 9, 538-541). Here, the following relations apply:

$$\frac{Q_A}{Q_a} + \frac{Q_B}{Q_b} = X$$

X=1 means additivity

X>1 means antagonism

X<1 means synergism $Q_a$=concentration of substance A which is the MIC $Q_b$=concentration of substance B which is the MIC $Q_A$=concentration of substance A in the concentration of A/B which suppresses the microbial growth $Q_B$=concentration of substance B in the concentration of A/B which suppresses the microbial growth Results:

|  | MIC against<br>Gloeophyllum trabeum (ppm) | Synergistic<br>value X |
|---|---|---|
| tebuconazole | 0.5 | — |
| tebuconazole/additive 1 (1:0.8) | 0.5 | 0.56 |
| tebuconazole/additive 1 (1:3.2) | 1.0 | 0.51 |
| tebuconazole/additive 1 (1:7.2) | 2.0 | 0.51 |
| additive 1 | >30[1)] | — |

[1)]up to 30 ppm, no inherent activity was noticed.

In the case of the wood-destroying fungus *Gloeophyllum trabeum*, tebuconazole and additive 1 show, at various mixing ratios, a pronounced synergism.

Example 2

Combination of Triadimefon and Amidoalkylamine Against the Wood-Destroying Fungus *Poria placenta*

Mycelium pieces were punched out of a colony of the wood-destroying fungus *Poria placenta* and incubated at 26° C. on a malt extract/peptone-containing nutrient agar. The hyphae growth with and without added active compound and/or additive was compared. The minimum inhibitory concentration (MIC) stated is the concentration at which the radial hyphae growth is suppressed completely.
Results:

|  | MIC against<br>Poria placenta (ppm) | Synergistic<br>value X |
|---|---|---|
| triadimefon | 3.0 | — |
| triadimefon/additive 1 (1:0.8) | 2.0 | 0.40 |
| additive 1 | >30[1)] | — |

[1)]up to 30 ppm, no inherent activity was noticed.

In the case of the wood-destroying fungus *Poria placenta*, triadimefon and additive 1 show synergistic activity.

Example 3

Combination of Propiconazole and Amidoalkylamine Against the Wood-Destroying Fungus *Poria placenta*

Mycelium pieces were punched out of a colony of the wood-destroying fungus *Poria placenta* and incubated at 26° C. on a malt extract/peptone-containing nutrient agar. The hyphae growth with and without added active compound and/or additive was compared. The minimum inhibitory concentration (MIC) stated is the concentration at which the radial hyphae growth is suppressed completely.
Results:

|  | MIC against<br>Poria placenta (ppm) | Synergistic<br>value X |
|---|---|---|
| propiconazole | 0.5 | — |
| propiconazole/additive 1 (1:0.8) | 0.7 | 0.79 |
| additive 1 | >30[1)] | — |

[1)]up to 30 ppm, no inherent activity was noticed.

In the case of the wood-destroying fungus *Poria placenta*, propiconazole and additive 1 show synergistic activity.

Example 4

Formulations and Efficacy Test

Formulation a) tebuconazole formulated as a ater-emulsifable concentrate (EC), comprising:
2.5% by weight of tebuconazole, 30% by weight of castor oil ethoxy late and 67.5% of 2,2,4-trimethyl-1,3-pentanediol mono(2-methylpropionate) (Texanol®), Formulation b) tebuconazole+additive 1 formulated as a water-emulsifiable concentrate (EC), comprising:
2.5% by weight of tebuconazole, 10% by weight of additive 1 (80% strength in water/propylene glycol), 30% of castor oil ethoxylate and 57.5% by weight of 2,2,4-trimethyl-1,3-pentanediol mono(2-methylpropionate) (Texanol®).

Similar to the Normtest EN113, formulations a) and b) were each examined for their efficacy in a test against wood-destroying fungi. Compared to the Normtest, smaller pieces of wood were used, and the woods were exposed to fungal attack for a shorter period of time (8 weeks).

To this end, dried test specimens (25×15×4 mm) of pine (*Pinus sylvestris*) were in each case vacuum-drenched with aqueous dilutions of formulations a) and b). Based on the concentration of tebuconazole in the drench solution and the uptake of the drench solution into the test specimens, the amount of active compound taken up by the test specimen (retention) was calculated. The test specimens were dried and then weighed. To prevent a misleading colonization by foreign pathogens, the test specimens were sterilized using gamma rays.

The test specimens were brought into contact with the wood-destroying fungus *Poria placenta* and stored for 8 weeks. The test woods were then cleaned, dried and weighed. The loss of mass was calculated. For each retention, the mean value of six test specimens was determined.

TABLE 1

| No. | Retention<br>tebuconazole<br>[g/m$^3$] | Retention<br>additive 1<br>[g/m$^3$] | Loss<br>of mass<br>[%] |
|---|---|---|---|
| 1 (untreated test specimen) | 0 | 0 | 23 |
| 2 (test specimen treated with the emulsion from formulation a) | 44 | 0 | 16 |
| 3 (test specimen treated with the emulsion from formulation b) | 42 | 134.4 | 1 |
| 4 (test specimen treated with the emulsion from formulation a) | 75 | 0 | 9 |
| 5 (test specimen treated with the emulsion from formulation b) | 76 | 243.2 | 0 |

The test in analogy to EN113 shows that, by using additive 1, the efficacy of tebuconazole is increased. At identical retention (i.e. the amount of active compound taken up by the wood) for tebuconazole, the loss of mass when using additive 1 is less than without.

Example 5

Formulations and Test for Efficacy

Formulation c) triadimefon formulated as a water-emulsifiable concentrate (EC) comprising:
2.5% by weight of triadimefon, 30% by weight of castor oil ethoxylate and 67.5% of 2,2,4-trimethyl-1,3-pentanediol mono(2-methylpropionate) (Texanol®), formulation d) triadimefon+additive 1 formulated as a water-emulsifiable concentrate (EC) comprising:
2.5% by weight of triadimefon, 10% by weight of additive 1 (80% strength in water/propylene glycol), 30% of castor oil ethoxylate and 57.5% by weight of 2,2,4-trimethyl-1,3-pentanediol mono(2-methylpropionate) (Texanol®).

As described in Example 4, formulations c) and d) were each examined for their efficacy in a test against wood-destroying fungi similar to the Normtest EN113.

The test specimens were brought into contact with the wood-destroying fungus Coniophora puteana and stored for 8 weeks. Evaluation was carried out as described in Example 4.

TABLE 2

| No. | Retention triadimefon [g/m³] | Retention additive 1 [g/m³] | Loss of mass [%] |
|---|---|---|---|
| 1 (untreated test specimen) | 0 | 0 | 32 |
| 2 (test specimen treated with the emulsion from formulation c) | 215 | 0 | 30 |
| 3 (test specimen treated with the emulsion from formulation d) | 217 | 694 | 22 |
| 4 (test specimen treated with the emulsion from formulation c) | 325 | 0 | 31 |
| 5 (test specimen treated with the emulsion from formulation d) | 321 | 1027 | 8 |

The test in analogy to EN113 shows that, by using additive 1, the efficacy of triadimefon is increased. At identical retention (i.e. the amount of active compound taken up by the wood) for triadimefon, the loss of mass when using additive 1 is less than without.

The invention claimed is:
1. A process for protecting an industrial materials against attack or destruction by microorganisms, comprising:
   contacting the microorganisms or a habitat of the microorganisms with a compound comprising
   a) at least one azole and
   b) at least one amidoalkylamine of the formula (I), a salt and/or acid addition compound thereof,

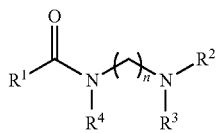

(I)

wherein
   $R^1$ represents optionally substituted $C_1$-$C_{40}$-alkyl or $C_2$-$C_{40}$-alkenyl,
   $R^2$, $R^3$ and $R^4$ independently of one another represent hydrogen or $C_1$-$C_8$-alkyl, and
   n represents an integer from 1 to 6,
   wherein the industrial material is wood, a timber product or a wood/plastic composite.

2. The process according to claim 1, wherein the azole is a triazole selected from the group consisting of azaconazole, bitertanol, bromuconazole, cyproconazole, diclobutrazol, difenoconazole, diniconazole, epoxyconazole, etaconazole, fenbuconazole, fluquinconazole, flusilazole, flutriafol, furconazole, hexaconazole, imibenconazole, ipconazole, myclobutanil, metconazole, penconazole, propiconazole, prothioconazole, simeconazole, tebuconazole, tetraconazole, triadimefon, triadimenol, triticonazole, uniconazole, metal salts thereof, and acid adducts thereof.

3. The process according to claim 1, wherein the azole is selected from the group consisting of tebuconazole, propiconazole, and cyproconazole.

4. The process according to claim 3, further comprising triadimenol or triadimefon.

5. The process according to claim 1, wherein
   $R^1$ represents $C_2$-$C_{36}$-alkyl or $C_2$-$C_{36}$-alkenyl,
   $R^2$, $R^3$ and $R^4$ independently of one another represent hydrogen or $C_1$-$C_4$-alkyl, and
   n represents a number from 1 to 4.

6. The process according to claim 1, wherein
   $R^1$ represents $C_5$-$C_{19}$-alkyl or $C_5$-$C_{19}$-alkenyl,
   $R^2$ and $R^3$ each represent methyl,
   $R^4$ represents hydrogen, and
   n represents 3.

7. The process according to claim 1, further comprising: a chelating agent present in an amount of 0.01 mol based on the compound of the formula (I).

8. The process according to claim 1 wherein said microorganism is a wood-destroying basidiomycetes.

9. The process according to claim 8, wherein the wood-destroying basidiomycetes is a holobasidiomycete.

10. The process according to claim 1, further comprising: a chelating agent present in an amount of less than 0.001 mol based on the compound of the formula (I).

11. A composition comprising:
    a) at least one azole selected from the group consisting of azaconazole, bitertanol, bromuconazole, cyproconazole, diclobutrazol, difenoconazole, diniconazole, epoxyconazole, etaconazole, fenbuconazole, fluquinconazole, flusilazole, flutriafol, furconazole, hexaconazole, imibenconazole, ipconazole, myclobutanil, metconazole, penconazole, propiconazole, prothioconazole, simeconazole, tebuconazole, tetraconazole, triticonazole, uniconazole, their metal salts, and their acid adducts;
    b) at least one amidoalkylamine of the formula (I), a salt and/or acid addition compound thereof,

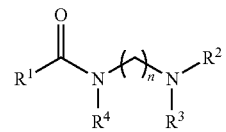

(I)

wherein
   $R^1$ represents optionally substituted $C_1$-$C_{40}$-alkyl or $C_2$-$C_{40}$-alkenyl,
   $R^2$, $R^3$ and $R^4$ independently of one another represent hydrogen or $C_1$-$C_8$-alkyl, and
   n represents an integer from 1 and 6,
   and further comprising triadimenol or triadimefon.

12. The composition according to claim 11, wherein the at least one azole is selected from the group consisting of tebuconazole, propiconazole, and cyproconazole.

13. An industrial material comprising
a) at least one azole and
b) at least one amidoalkylamine of the formula (I), a salt and/or acid addition compound thereof,

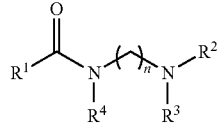
(I)

wherein
$R^1$ represents optionally substituted $C_1$-$C_{40}$-alkyl or $C_2$-$C_{40}$-alkenyl,
$R^2$, $R^3$ and $R^4$ independently of one another represent hydrogen or $C_1$-$C_8$-alkyl, and
n represents an integer from 1 to 6,
wherein said industrial material is wood, a timber product or a wood/plastic composite.

* * * * *